United States Patent [19]

Baker et al.

[11] Patent Number: 4,992,436

[45] Date of Patent: Feb. 12, 1991

[54] SPIRO-AZABICYCLIC MUSCARINIC AGONISTS

[75] Inventors: Raymond Baker, Much Hadham; Leslie J. Street, Harlow; John Saunders, Bishops Stortford, all of England

[73] Assignee: Merck Sharp & Dohme, Ltd., Hertfordshire, England

[21] Appl. No.: 373,001

[22] Filed: Jun. 29, 1989

[30] Foreign Application Priority Data

Jul. 8, 1988 [GB] United Kingdom ............... 8816299

[51] Int. Cl.$^5$ ................... A61K 31/395; C07D 497/20
[52] U.S. Cl. .................... 514/215; 540/543; 546/18; 546/19; 514/278
[58] Field of Search ................ 546/18, 19; 540/543; 514/215, 278

[56] References Cited

U.S. PATENT DOCUMENTS 4,104,397  8/1978  Cohen et al. ................... 546/18
4,855,290  8/1989  Fisher et al. ................... 514/278

*Primary Examiner*—Robert T. Bond
*Attorney, Agent, or Firm*—Manfred Polk; Joseph F. DiPrima

[57] ABSTRACT

The present invention provides a spiro-azabicyclic compound or a salt or prodrug thereof, said compound comprising a saturated or unsaturated 5-membered heterocyclic ring containing two heteroatoms selected from oxygen, nitrogen and sulphur, no more than one of said heteroatoms being nitrogen; said heterocyclic ring having a spiro attachment to an optionally substituted azabicyclo[2.2.1]heptane or azabicyclo[3.2.1]octane ring system; which compounds are useful for the treatment of neurological and mental disorders.

6 Claims, No Drawings

SPIRO-AZABICYCLIC MUSCARINIC AGONISTS

The present invention relates to a class of substituted spiro-azabicyclic derivatives which are capable of enhancing muscarinic cholinergic transmission in the cortex and are therefore useful in the treatment of neurological and mental illnesses whose clinical manifestations are attributable to a deficiency in central cholinergic function. Such diseases include presenile and senile dementia (also known as Alzheimer's disease and senile dementia of the Alzheimer type respectively), Huntington's chorea, tardive dyskinesia, hyperkinesia, mania and Tourette Syndrome. Alzheime's disease, the most common dementing illness, is a slowly progressive neurological disorder characterised by marked deficits in cognitive functions including memory, attention, language and visual perception capabilities.

Spiro-dioxolane and spiro-oxathiolane derivatives of quinuclidine having muscarinic agonist activity are described in U.S. Pat. No. 4,104,397 and EP-A-0205247 respectively. The corresponding derivatives of azacyclic systems such as piperidine, as well as the spiro-dithiolane derivatives thereof, are also known to have muscarinic agonist activity (see, for example, EP-A-0189370 and J. Saunders et al., *J. Med. Chem.*, 1988, 31, 486). These compounds act by stimulating cholinergic transmission.

These prior art compounds do, however, display only marginal, if any, selectivity for binding to muscarinic receptors located in the brain rather than to those located in peripheral tissues such as the heart (see, for example, J. Saunders et al., *J. Med. Chem.*, 1987, 30, 969). In contrast to this, the spiro-azabicyclic derivatives of the present invention have been found to possess a significant selective affinity for muscarinic receptors located in the brain, and particularly those in the cortex. In view of these effects, the compounds of the present invention are of benefit in the treatment of Alzheimer's disease and related diseases of cholinergic dysfunction by reversing the cholinergic deficiency, whilst at the same time being responsible for a significantly reduced incidence of the undesirable peripherally-mediated side-effects normally associated with muscarinic cholinergic ligands.

The present invention thus provides a spiro-azabicyclic compound or a salt or prodrug thereof, said compound comprising a saturated or unsaturated 5-membered heterocyclic ring containing two heteroatoms selected from oxygen, nitrogen and sulphur, no more than one of said heteroatoms being nitrogen; said heterocyclic ring having a spiro attachment to an optionally substituted azabicyclo[2.2.1]heptane or azabicyclo[3.2.1]octane ring system.

In particular, the compounds according to the invention may be represented by formula I:

wherein Q represents the residue of an optionally substituted azabicyclo[2.2.1]heptane or azabicyclo[3.2.1]octane ring system; and T represents the residue of a saturated or unsaturated 5-membered heterocyclic ring containing two heteroatoms selected from oxygen, nitrogen and sulphur, no more than one of said heteroatoms being nitrogen.

Specifically, the invention provides a compound of formula IA:

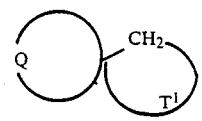

or a salt or prodrug thereof; wherein
Q is as defined above; and
—$T^1$— represents a group of formula

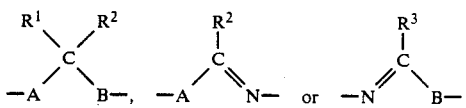

in which A and B independently represent oxygen or sulphur;
$R^1$, $R^2$ and $R^3$ independently represent hydrogen, —$OR^4$, or an optionally substituted saturated or unsaturated hydrocarbon group; and
$R^4$ represents $C_{1-4}$ alkyl, $C_{2-4}$ alkenyl or $C_{2-4}$ alkynyl.

In formula IA above, therefore, the 5-membered heterocyclic ring containing the substituents A and/or B may be a 1,3-dioxolane, 1,3-dithiolane, 1,3-oxathiolane, oxazoline or thiazoline ring. Preferably, the 5-membered ring is a 1,3-dioxolane ring, i.e. a ring in which A and B both represent oxygen.

The substituent Q in formulae I and IA is suitably the residue of an optionally substituted 1- or 2-azabicyclo[2.2.1]heptane ring system or of an optionally substituted 1-azabicyclo[3.2.1]octane ring system, and may conveniently be represented by structures (i), (ii), (iii) or (iv) as follows:

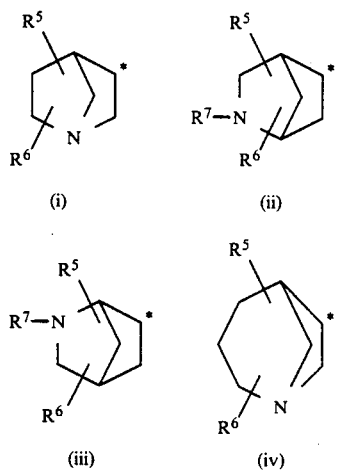

wherein
$R^5$ and $R^6$ independently represent hydrogen, $C_{1-4}$ alkyl, halogen, $C_{1-4}$ alkoxy, hydroxy or carboxy, or $R_5$ and $R_6$ together represent a carbonyl group;
$R_7$ represents hydrogen, $C_{1-6}$ alkyl, $C_{2-6}$ alkenyl or $C_{2-6}$ alkynyl; and
the asterisk represents the point of spiro attachment of the 5-membered heterocyclic ring.

It is to be understood that the $R^5$ and $R^6$ substituents may independently be attached to any carbon atom in the azabicyclic ring system except the spiro carbon atom marked with an asterisk. Moreover, when $R^5$ and $R^6$ together represent a carbonyl group, this substituent may additionally not be attached to the bridgehead carbon atom(s).

It will be appreciated that the nitrogen atom in the azabicyclic ring system will carry a lone pair of electrons.

Suitably the group $R^5$ is hydrogen or methyl; and $R^6$ is hydrogen, methyl, fluoro or hydroxy. Suitably at least one of $R^5$ and $R^6$ is hydrogen. Preferably both $R^5$ and $R^6$ are hydrogen.

A preferred ring system for Q is the 1-azabicyclo2.2.1]heptane system as depicted in structure (i) above.

When $R^1$, $R^2$ or $R^3$ represents an optionally substituted saturated or unsaturated hydrocarbon group it may suitably be $C_{1-8}$ alkyl, $C_{2-8}$ alkenyl, $C_{2-8}$ alkynyl, aryl or aralkyl. The hydrocarbon group may carry one or more substituents. Suitable substituent groups for the hydrocarbon groups $R^1$, $R^2$ and $R^3$ include halogen, hydroxy, —$OR^4$, —$CF_3$, —$NR^4R^8$ or optionally substituted aryl; wherein $R^4$ is as defined above, and $R^8$ represents hydrogen, $C_{1-4}$ alkyl, $C_{2-4}$ alkenyl, $C_{2-4}$ alkynyl or acetyl.

The alkyl, alkenyl or alkynyl groups mentioned herein may be straight-chained, branched or cyclic groups. It will be appreciated that any branched or cyclic groups will contain 3 or more carbon atoms. In particular, the alkyl groups may be optionally substituted methyl or ethyl, or optionally substituted straight-chained or branched propyl, butyl, pentyl or hexyl. Suitable cyclic groups include optionally substituted cyclopropyl, cyclopentyl or cyclohexyl.

When used herein the term "aryl" includes phenyl and naphthyl optionally substituted with up to five, preferably up to three, groups suitably selected from halogen, $C_{1-6}$ alkyl, —$OR_4$, —$CF_3$, $C_{2-6}$ alkoxycarbonyl, —$NO_2$ and —$NR_4R_8$; wherein $R^4$ and $R^8$ are as defined above.

The term "halogen" includes, for example, fluorine, chlorine, bromine and iodine.

Suitably, $R^1$ and $R^2$ independently represent hydrogen, methyl or ethyl. In a preferred embodiment, one of $R^1$ and $R^2$ represents hydrogen and the other represents methyl or ethyl.

One sub-class of compounds within the scope of the present invention is represented by formula II:

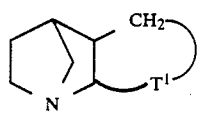
(II)

wherein $T^1$ is as defined above.

Preferred compounds according to the invention are those compounds of formula II wherein —$T^1$— represents a group of formula

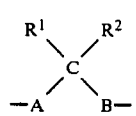

in which A, B, $R^1$ and $R^2$ are as defined above. Of these compounds, particularly preferred are those represented by structures IIA and IIB:

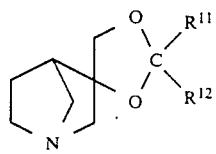 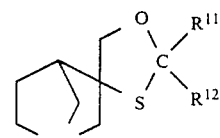
(IIA)            (IIB)

wherein $R^{11}$ and $R^{12}$ independently represent hydrogen, straight-chained or branched $C_{1-4}$ alkyl, $C_{3-6}$ cycloalkyl or phenyl. More particularly preferred are those compounds of formula IIA wherein one of $R^{11}$ and $R^{12}$ represents hydrogen and the other represents methyl or ethyl.

Also preferred according to the invention are those compounds of formula II wherein —$T^1$— represents a group of formula

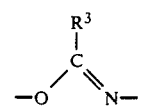

i.e. those compounds having the structure IIC:

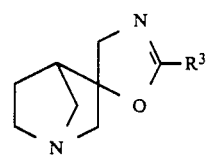
(IIC)

in which $R^3$ is as defined above, but preferably represents methyl.

A further sub-class of compounds within the scope of the present invention is represented by formula III:

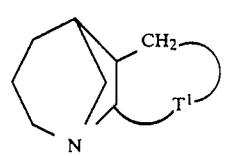
(III)

wherein $T^1$ is as defined above.

Preferred compounds according to the invention are those compounds of formula III wherein —$T^1$— represents a group of formula

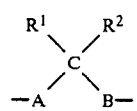

in which A, B, $R^1$ and $R^2$ are as defined above. Of these compounds, particularly preferred are those represented by structure IIIA:

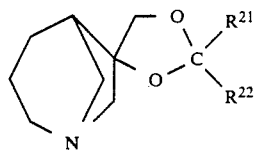
(IIIA)

wherein $R^{21}$ and $R^{22}$ independently represent hydrogen, straight-chained or branched $C_{1-4}$ alkyl, $C_{3-6}$ cycloalkyl or phenyl. More particularly preferred are those compounds of formula IIIA wherein one of $R^{21}$ and $R^{22}$ represents hydrogen and the other represents methyl or ethyl.

Specific compounds within the scope of the present invention include:
2'-methylspiro[1-azabicyclo[2.2.1]heptane-3,4'-[1,3]dioxolane];
2'-ethylspiro[1-azabicyclo[2.2.1]heptane-3,4'-[1,3]dioxolane];
2'-propylspiro[1-azabicyclo[2.2.1]heptane-3,4'-[1,3]dioxolane];
2'-(1-methylethyl)spiro[1-azabicyclo[2.2.1]heptane-3,4'-[1,3]dioxolane];
2'-cyclopropylspiro[1-azabicyclo[2.2.1]heptane-3,4'-[1,3]dioxolane];
2'-phenylspiro[1-azabicyclo[2.2.1]heptane-3,4'-[1,3]dioxolane];
2',2'-dimethylspiro[1-azabicyclo[2.2.1]heptane-3,4'-[1,3]dioxolane];
2'-methylspiro[1-azabicyclo[2.2.1]heptane-3,4'-[1,3]oxathiolane];
2'-ethylspiro[1-azabicyclo[2.2.1]heptane-3,4'-[1,3]oxathiolane];
2'-methylspiro[1-azabicyclo[2.2.1]heptane-3,5'-[1,3]oxazoline];
2'-methylspiro[1-azabicyclo[3.2.1]octane-6,4'-[1,3]dioxolane];
and salts and prodrugs thereof.

Most of the compounds of this invention have at least two asymmetric centres and often more than two; and can therefore exist as both enantiomers and diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful in the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid and phosphoric acid. Where the novel compound carries a carboxylic acid group the invention also contemplates salts thereof, preferably non-toxic pharmaceutically acceptable salts thereof, such as the sodium, potassium and calcium salts thereof.

The method of treatment of this invention includes a method of treating Alzheimer's disease, senile dementia of the Alzheimer type, Huntington's chorea, tardive dyskinesia, hyperkinesia, mania or Tourette syndrome by the administration to a patient in need of such treatment of an effective amount of one or more of the novel compounds.

This invention therefore also provides a pharmaceutical composition comprising a compound of the invention and a pharmaceutically acceptable carrier.

It may, where appropriate, be advantageous, in order to reduce unwanted peripherally mediated side-effects, to incorporate into the composition a peripherally acting cholinergic antagonist (or anti-muscarinic agent). Thus the compounds of the invention may advantageously be administered together with a peripheral cholinergic antagonist such as N-methylscopolamine, N-methylatropine, propantheline, methantheline or glycopyrrolate.

The compounds of the invention can be administered orally, parenterally or rectally at a daily dose of about 0.01 to 10 mg/kg of body weight, preferably about 0.1 to 1 mg/kg, and may be administered on a regimen of 1 to 4 times a day. When a cholinergic antagonist is administered, it is incorporated at its conventional dose.

The pharmaceutical formulations of this invention preferably are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The oxazoline and thiazoline compounds of the present invention may be prepared by a process which comprises reacting a reactive derivative of a carboxylic acid of formula $R^3$—$CO_2H$ with a compound either of formula IV or of formula V or a salt thereof:

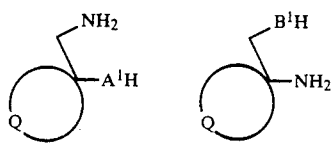

(IV)   (V)

wherein $A^1$ and $B^1$ are oxygen or sulphur; and Q and $R^3$ are as hereinbefore defined.

Suitable reactive derivatives of the acid $R^3$—$CO_2H$ include esters, for example $C_{1-4}$ alkyl esters; thioesters, for example pyridylthioesters; acid anhydrides, for example $(R^3CO)_2O$; acid halides, for example acid chlorides; orthoesters; and primary, secondary and tertiary amides.

A preferred reactive derivative of the acid $R^3$—$CO_2H$ is the iminoether derivative of formula VI:

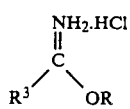

(VI)

wherein R is $C_{1-4}$ alkyl.

The process is conveniently effected by condensation of the starting materials in the presence of thionyl chloride, phosphorus oxychloride or triphenylphosphine/diethyl azodicarboxylate.

The intermediates of formula IV may be prepared by conventional methods, for example:

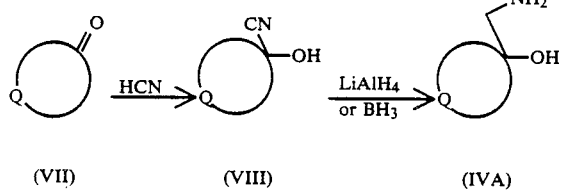

(VII)   (VIII)   (IVA)

The 1,3-dioxolanes, 1,3-dithiolanes and 1,3-oxathiolanes of the present invention may be prepared by reaction of a carbonyl compound of formula IX:

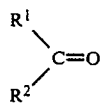

(IX)

wherein $R^1$ and $R^2$ are as hereinbefore defined; or a reactive derivative thereof, e.g. the dimethyl acetal derivative; with a compound of formula X:

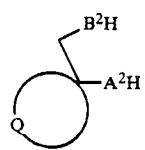

(X)

wherein Q is as hereinbefore defined; and $A^2$ and $B^2$ independently represent oxygen or sulphur. The reaction is suitably carried out in the presence of acid in an inert solvent such as benzene, toluene or The preparation of the intermediate of formula X, in which $A^2$ and $B^2$ are both oxygen, from compound VIII is illustrated by the following sequence:

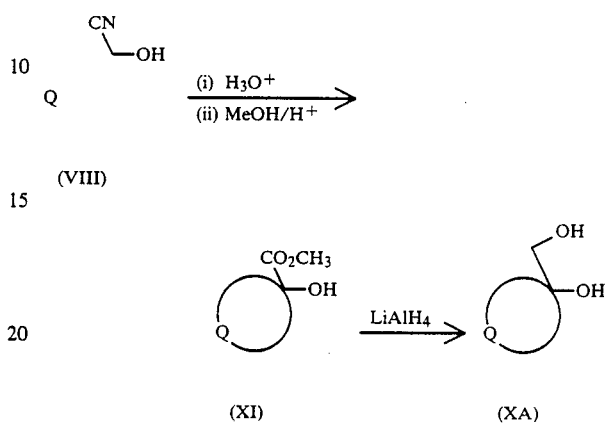

(VIII)

(XI)   (XA)

An alternative method for the preparation of the intermediate of formula XI, which may, for example, be useful in the preparation of alternative stereoisomers of the intermediate of formula X, commences from the intermediate of formula VII and may be illustrated as follows:

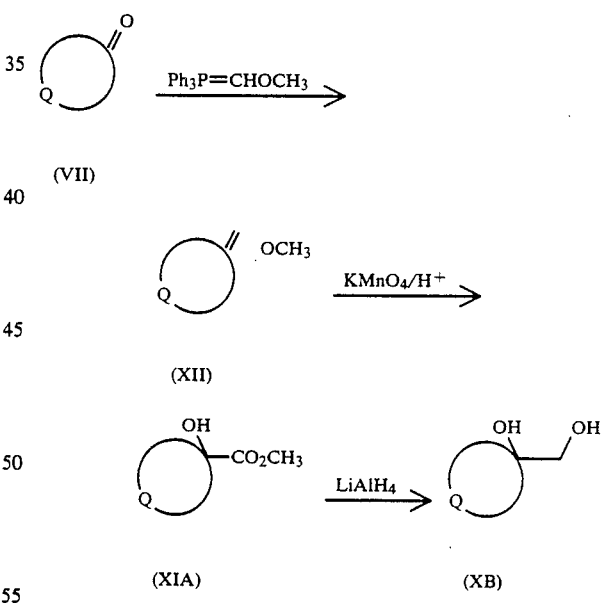

(VII)

(XII)

(XIA)   (XB)

The preparation of the intermediate of formula X where $A^2$ is oxygen and $B^2$ is sulphur is illustrated by the following sequence:

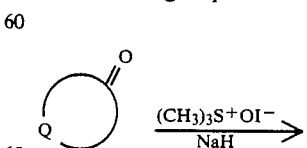

(VII)

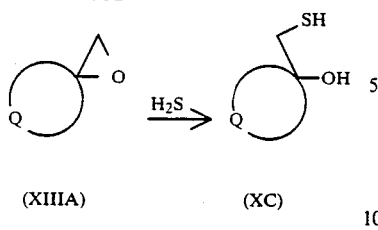

An alternative method for the preparation of the intermediate XIII, which may, for example, be useful in the preparation of alternative stereoisomers of the intermediate of formula X, may be illustrated as follows:

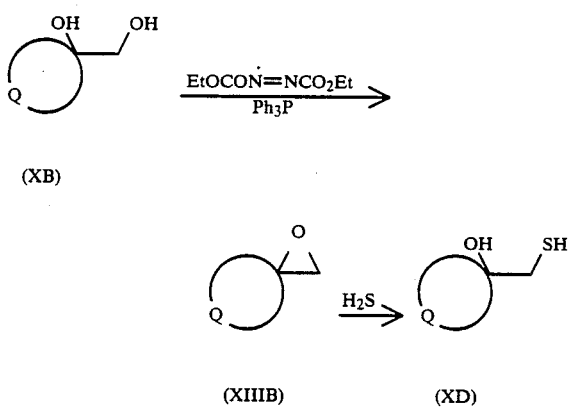

The preparation of the intermediate of formula X where $A^2$ is sulphur and $B^2$ is oxygen is illustrated by the following sequence:

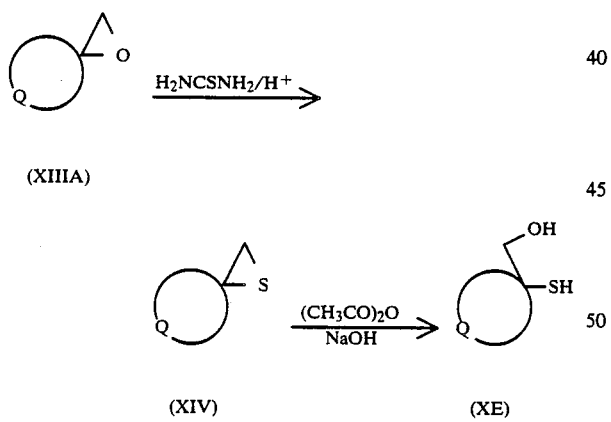

The preparation of the intermediate of formula X where $A^2$ and $B^2$ are both sulphur is illustrated by the following sequence:

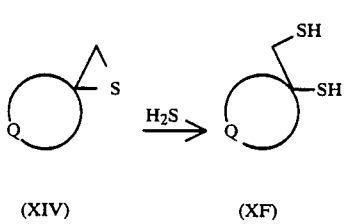

The azabicyclo[2.2.1]heptanones and azabicyclo[3.2.1]octanones of formula VII may be prepared by methods analogous to those described in EP-A-0239309.

In any of the above reactions it may be necessary and/or desirable to protect any sensitive groups in the compounds. For example, if the substituents include amino, carboxy, hydroxy or thiol groups, these may be protected in conventional manner. Thus, suitable protecting groups for hydroxy groups include silyl groups such as trimethylsilyl or t-butyldimethylsilyl and etherifying groups such as tetrahydropyranyl; and for amino groups include benzyloxycarbonyl and t-butoxycarbonyl. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention. Each of the compounds of the Examples demonstrates an affinity for the muscarinic receptor, having an $IC_{50}$ (concentration required to displace 50% of specific $[^3H]$-N-methylscopolamine binding from rat cortical membrane preparations) significantly lower than 100 $\mu$M. Penetrability into the central nervous system of compounds of this invention was assessed by a measurable displacement of radioligand binding using standard "ex-vivo" binding techniques (Ref: *J. Neurosurg.*, 1985, 63, 589–592). Functional selectivity of the compounds was assessed in in vitro assays such as rat superior cervical ganglion, and guinea pig ileum and atrium, as described, for example, in J. Saunders et al., *J. Med. Chem.*, 1987, 30, 969.

In the Examples, all temperatures are in °C; THF is tetrahydrofuran; and ether is diethyl ether.

EXAMPLE 1

2'(R*)-Methyl-4(R*)-spiro[1-azabicyclo[2.2.1]heptane3(R*),4'-[1,3]dioxolane] hydrochloride and 2'(S*)-Methyl-4(R*)-spiro[1-azabicyclo[2.2.1]heptane3(R*),4'-[1,3]dioxolane] hydrochloride

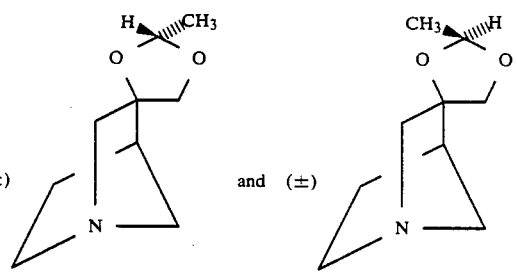

(a) Methyl 3(R*)-hydroxy-4(R*)-1-azabicyclo [2.2.1]heptan-3-carboxylate

1-Azabicyclo[2.2.1]heptan-3-one (1.5 g, 10.3 mmol) in methanol (5 ml) was treated with ethereal hydrogen chloride and the solvents evaporated. The hydrochloride in water (4 ml) was cooled to $-10°$ C. and sodium cyanide (0.51 g, 10.4 mmol) in water (4 ml) added dropwise keeping the temperature below $+10°$ C. After a further hour at 0° C., the precipitated cyanohydrin was collected by filtration and washed with cold water. This material in concentrated HCl (14 ml) was stirred at 20° C. for 4 days before exhaustively evaporating the solution to dryness. The residue was treated with anhydrous methanolic hydrogen chloride for 24 hours and the mixture again evaPorated. The residue was taken up into water, the solution basified to pH 10 with solid Potassium carbonate and then extracted with dichloromethane. Evaporation of the organic extracts followed by chromatography on alumina in dichloromethane/methanol (97:3) afforded the desired hydroxyester as a white solid (1.3 g); m.p. 150°-152°; $R_f=0.4$ in dichloromethane/methanol (19:1) on alumina; (Found: $M^+$ 171.0874 $C_8H_{13}NO_3$ requires $M^+ = 171.0854$); $\delta$ (360 MHz, $CDCl_3$) 1.38–1.48 and 2.16–2.21 (each 1H, each m, $CH_2$); 2.40–2.49 and 2.66–2.73 (4H, each m, 4-CH, one of $CH_2N$ and $CH_2N$); 2.91–3.26 (3H, m, $NCH_2CO$ and one of $CH_2N$) and 3.82 (3H, s, $OCH_3$).

(b) 2'(R*)-Methyl-4(R*)-spiro[1-azabicyclo[2.2.1-]heptane-3(R*),4'-[1,3]dioxolane] hydrochloride and 2'(S*)-Methyl-4(R*)-spiro[1azabicyclo[2.2.]heptane-3(R*),4'-[1,3]dioxolane] hydrochloride.

A solution of the foregoing hydroxyester (1.3 g, 7.6 mmol) in tetrahydrofuran (50 ml) was added dropwise to a stirred suspension of $LiAlH_4$ 10.97 g. 25.5 mmol) in tetrahydrofuran (50 ml). After 1.5 hours at 70° C., the mixture was stirred at 20° C. for 1.5 hours and cooled to 10° C. Excess reducing agent was destroyed by the successive dropwise addition of ethyl acetate (1 ml), water (1 ml), 15% aqueous sodium hydroxide (1 ml) and water (1 ml). The mixture was filtered and the material isolated from the filtrate was purified by chromatography on alumina with dichloromethane-methanol (3:1) to yield the intermediate diol (0.5 g); $\delta$ (360 MHz, $CD_3OD$) 1.45–1.54 and 2.1014 2.16 (each 1H, each m, $CH_2$); 2.20–2.25 and 2.39–2.42 ) each 1H, each m, $CH_2N$); 2.52 (1H, d, J=3.9 Hz, 4-CH); 2.63–2.88 (4H, m, 2 x $CH_2N$) and 3.37 and 3.49 (each 1H, each d, each J=11.4 Hz, $CH_2O$). All of this material in dichloromethane (4 ml) was treated at 0° C. with acetaldehyde (2 ml) and then boron trifluoride etherate (2 ml). After 1.5 hour at 5° C., the mixture was poured on to 20% aqueous potassium hydroxide solution (12 ml) and stirred at 5° C. for 0.25 hour. The aqueous solution was exhaustively extracted with dichloromethane and the residue isolated from the organic extracts purified by chromatography on alumina. Using a gradient elution (from ethyl acetate to 5% methanol in ethyl acetate), two pure components were isolated. Isomer A, the less polar product on TLC (110 mgs. $R_f=0.6$ on alumina in dichloromethane-methanol, 19:1) was treated with an excess of ethereal hydrogen chloride and the resulting solid recrystallised from isopropanol-ether to afford the hydrochloride salt of a single diastereomer, m.p. 175°-178° C.; (Found: C, 52.21; H, 7.58; N, 6.82. $C_9H_{15}NO_2$ HCl requires C, 52.55; H, 7.79; N, 6.82%); m/e 170 $(M+1)^+$; $\delta$ (360 MHz, $D_2O$) 1.40 (3H, d, J=4.9 Hz, $CH_3$); 2.04–2.16 and 2.24–2.39 (each 1H, each m, 5-$CH_2$); 3.08 (1H, d, J=4.1 Hz. 4-CH); 3.24–3.38, 3.48–3.59 and 3.64–3.69 (6H, each m, 3 x $CH_2N$); 3.97 and 4.13 (each 1H, each d, each J=8.6 Hz, $CH_2O$) and 5.22 (1H, q, J=4.9 Hz, $CHCH_3$).

The slower running isomer (210 mgs), that is the more polar diastereomer on TLC ($R_f=0.55$), was treated exactly as described above for isomer A to yield the hydrochloride salt of isomer B, m.p. 202°-206° C.; (Found: C, 52.99; H, 7.73; N, 6.74. $C_9H_{15}NO_2$. HCl requires C, 52.55; H, 7.79; N, 6.82%); m/e 170 $(M+1)^+$; $\delta$ (360 MHz. $D_2O$) 1.40 (3H, d, J=4.9 Hz. $CH_3$); 2.04–2.16 and 2.28–2.42 (each 1H, each m, 5-$CH_2$); 2.90 (1H, d, J=4.1 Hz, 4-CH); 3.29–3.42 and 3.48–3.59 (6H, each m, 3 x $CH_2N$); 3.84 and 4.32 (each 1H, each d, each J=9.4 Hz, $CH_2O$) and 5.20 (1H, q, J=4.9 Hz, $CHCH_3$).

EXAMPLE 2

2'(RS)-Methyl-4(R*)-spiro[1-azabicyclo2.2.1] heptane-3(S*),4'-[1,3]dioxolane]

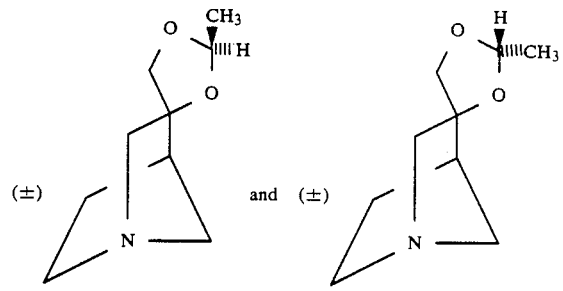

(a) Methyl 3(S*)-Hydroxy-4(R*)-1-azabicyclo [2.2.1]heptane-3-carboxylate

1-Azabicyclo[2.2.1]heptane-3-one (4.3 g, 39 mmol) in THF (100 ml) was stirred over activated molecular sieve for 1 hour. Meanwhile, methoxymethyltriphenyl phosphonium chloride (19.8 g, 58 mmol) suspended in ether (200 ml) was treated at 0° to 10° C. with phenyl lithium (29 ml of a 2M solution in cyclohexane-diethyl ether, 70:30; 58 mmol). After stirring at 20° for 45 mins. the mixture was cooled to −60° and the dried ketone solution from above added droPwise at this temperature. The mixture was allowed to warm to 20°, filtered through Hyflo and the filtrate evaporated. Distillation of the residue gave the intermediate methyl enol ether as a colourless oil (4.2 g), b.p. 47°-50° C. at 0.1 mmHg; m/z 139 (M ); $\delta$ (360 MHz, $CDCl_3$) 1.33–1.42 and 1.68–1.79 (each 1H, each m, $CH_2$); 2.33–2:55 (3H, m, $NCH_2$ and 4-CH); 2.83–2.98 (2H, m, $CH_2N$); 3.28–3.43 (2H, m, $NCH_2C=$); 3.53 and 3.55 (3H, each s, OCH ) and 5.68 and 5.98 (1H, each m, CH=).

To the foregoing enol ether (2.8 g, 20 mmol) in 1M sulphuric acid (40 ml) was added potassium permanganate (400 ml of a 0.1M solution in water, 40 mmol) at such a rate as to achieve a slight permanent purple coloration. The mixture was filtered through Hyflo to remove the resultant manganese dioxide and the aqueous filtrates freeze dried. The resulting white powder was taken into anhydrous methanol (500 ml) to which thionyl chloride (10 ml) had previously been added at −20° C. After 16 hours at 20° C. the solution was evaporated and the residue in dichloromethane treated with saturated aqueous potassium carbonate solution. The material isolated from the organic layer was recrystallised from ethyl acetate to yield the title compound as a white solid (405 mg); mp 98°-99°; $R_f=0.4$ in methanol-dichloromethane (1:19) on alumina; (Found: $M^+ = 171.0884$. $C_8H_{13}NO_3$ requires $M^+ = 171.0854$); $\delta$ (360 MHz, $CDCl_3$) 1.23–1.31 and 1.44–1.53 (each 1H, each m, $CH_2$); 2.38–2.55 (3H, m, $CH_2N$ and one of $CH_2N$); 2.75–2.86 (2H, m, 4-CH and one of $CH_2N$); 2.99–3.02 and 3.14–3.19 (each 1H, each m, $CH_2$-COH) and 3.80 (3H, s, $OCH_3$).

(b) 2'(RS)-Methyl-4(R*)-spiro[1-azabicyclo2.2.1] heptane-3(S*),4'-[1.3]dioxolane].

The foregoing hydroxyester (1.5 g, 8.8 mmol) in THF (50 ml) was treated at room temperature with lithium aluminium hydride solution (12.4 ml of a 1M solution in THF, 12.4 mmol). After 16 hours, excess reducing was destroyed and the reaction mixture worked up exactly as described in Example 1(b) above. The intermediate diol was treated with acetaldehyde and boron trifluoride etherate also as given above and the crude product purified by chromatography on alumina in ethyl acetate to yield the diastereomers named in the title, $R_f=0.6$ in dichloromethane-methanol (19:1) on alumina; (Found: $M^+ = 169.1123$ $C_9H_{15}NO_2$ requires $M^+ = 169.1103$); δ (360 MHz, CDCl$_3$) 1.44 (3H, d, J=4.9 Hz, CH$_3$); 1.59–1.72 (2H, m, CH$_2$); 2.40–2.79 and 2.92–3.01 (7H, each m, 3 x CH$_2$N and 4-CH); 3.71, 3.86, 4.02 and 4.12 (each 0.5H, each d, J=8.1 and 8.4 Hz, OCH$_2$ of each diastereomer) and 4.99–5.06 (1H, m, CHCH$_3$).

EXAMPLE 3

2′(R*)-Ethyl-4(R*)-spiro[1-azabicyclo[2.2.1] heptane-3(S*), 4′-[1,3]dioxolane] hydrogen oxalate and 2′(S*)-ethyl-4(R*)-spiro(1-azabicyclo[2.2.1] heptane-3(S*), 4′-[1,3]dioxolane hydrogen oxalate

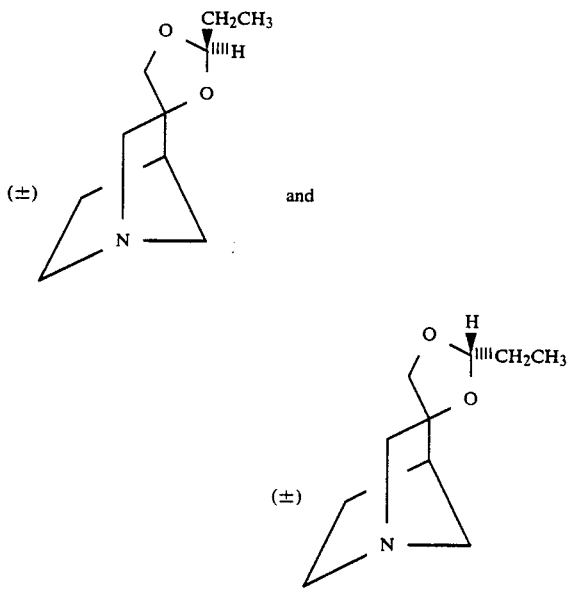

(a) Propionaldehyde diethyl acetal (1.32 g, 10 mmol) was added to a solution of the diol (360 mg, 2.52 mmol), prepared as described in Example 2(b) above, and anhydrous (±) camphor-10-sulphonic acid (812 mg, 3.5mmol) in dioxane (40 ml), and the mixture stirred at reflux for 5 hours. The resulting solution was allowed to stand overnight at room temperature, evaporated and the residue partitioned between saturated aqueous sodium carbonate and dichloromethane. The residue isolated from the organic layer was purified by chromatography on silica gel with 10–15% methanol in dichloromethane to give the diastereomers named in the title as a colourless gum (248 mg).

(b) A solution of the foregoing mixture of diastereomers (225 mg, 1.23 mmol) in THF (10 ml) was treated at −40° with borane in THF (1M; 1.5 ml). After 10 minutes, methanol (1 ml) was added, the mixture evaporated, and the residue chromatographed on silica gel with a gradient of 20–50% ethyl acetate in 60°–80° petroleum spirit, giving, in order of elution: fraction A - colourless gum (65 g) δ (360 MHz, CDCl$_3$) 0.94 (3H, t, J=7.5 Hz, CHCH$_2$CH$_3$), 1.50–1.58 (1H, m, 5-endo H), 1.6214 1.69 (2H, m, CHCH$_2$CH$_3$), 1.97–2.07 (1 H, m, 5-exo-H), 2.62 (1H, d, J=4.9 Hz, 4-H), 2.75–2.82 (2H, m, 6-endo H and 7anti-H), 2.89 (1H, dd, J=13.1, 2.6 Hz, 2-endo H), 3.05–3.14 (1H, m, 6-exo-H), 3.31–3.35 (2H. m, 2-exo H and 7-syn H), 3.77 (1 H, d, J=8.6 Hz, 3-syn H), 4.06 (1H, d, J=8.6 Hz, 3-anti H), 4.90 (1H, t, J=4.6 Hz, —CHCH$_2$CH$_3$), and fraction B as a colourless gum (106 mg), δ (360 MHz, CDCl$_3$) 0.94 (3H, t, J=7.5 Hz, —CHCH$_2$CH$_3$), 1.47–1.55 (1H, m, 5-endo H), 1.65–1.71 (2H, m, —CHCH$_2$CH$_3$), 1.96–2.03 (1H, m, 5-exo H), 2.63 (1 H, d, J=4.9 Hz, 4-H), 2.74–2.80 (2H, m, 6-exo H and 7-anti H), 2.93 (1H, dd, J=13.2, 2.7 Hz, 2-endo H), 3.06–3.14 (1H, m, 6-endo H), 3.24 (1H, br d, J=8.8 Hz, 7-syn H), 3.28 (1H, dd, J=13.4, 3.0 Hz, 2-exo H), 3.93 (2H, s, 3-H), 4.86 (1H, t, J=4.6 Hz, —CHCH$_2$CH$_3$).

Some mixed fractions (27 mg) were also obtained.

(c) Fraction A (60 mg) in ethylene glycol (1 ml) containing sodium methoxide (30 mg) was stirred for 1.5 hours at 160°, the solution cooled, diluted with water (10 ml) and extracted exhaustively with dichloromethane. The organic extracts were dried over anhydrous sodium carbonate and evaporated. The residue so obtained was redissolved in diethyl ether and a solution of anhydrous oxalic acid (30 mg) in ether added. The solid so produced was collected and recrystallised from methanol/ether to give (±)-2′(S*)-ethyl-4(R*)-spiro[1-azabicyclo[2.2.1]heptane-3(S*), 4′-[1,3]dioxolane] hydrogen oxalate as colourless plates (50 mg), m.p. 117°–119°; $R_f=0.53$ on silica gel in dichloromethane/methanol/ammonia (80:20:1); (Found: C. 52.77; H, 6.97; N, 5.09.C$_{12}$H$_{19}$NO$_6$ requires: C, 52.74; H, 7.01; N, 5.13%); m/e 184 (M+1)$^+$; δ (360 MHz, D$_2$O) 0.92 (3H, t, J=7.5 Hz, —CHCH$_2$CH$_3$), 1.65–1.72 (2H, m, —CHCH$_2$CH$_3$), 1.72–1.80 (1H, m, 5-endo H), 2.15–2.25 (1H, m, 5-exo H), 2.98 (1H, d, J=4.9 Hz, 4-H), 3.19–3.26 (1H, m, 6-endo H), 3.33 (1H, dd, J=9.3. 2.4 Hz, 7-syn H), 3.39–3.47 (2H, m, 2-endo H, 6-exo H), 3.60 (1H, br,d, J=9.3 Hz, 7-anti H), 3.67 (1H, dd, J=13.0, 2.8 Hz, 2-exo H), 4.02 (1H, d, J=9.3 Hz, 3′-anti H), 4.27 (1H, d, J=9.3 Hz, 3′-syn H). 5.05 (1H, t, J=4.7 Hz, —CHCH$_2$CH$_3$).

Fraction B (100 mg) was treated in a manner analogous to that described for fraction A above to afford (±)-2′-(R*)-ethyl-4(R*)-spiro[1-azabicyclo [2.2.1]heptane-3(S*). 4′-[1,3]dioxolane] hydrogen oxalate as colourless plates (84 mg), m.p. 106°–107°; R$_f$0.59 on silica gel in dichloromethane/methanol/ammonia (80:20:1); (Found: C, 52.55; H, 6.94; N, 5.11.C$_{12}$H$_{19}$NO$_6$ requires: C, 52.74; H, 7.01; N, 5.13%); m/e 184 (M+1)$^+$; δ (360 MHz, D$_2$O) 0.91 (3H, t, J=7.5 Hz, —CHCH$_2$CH$_3$), 1.66–1.75 (3H, m, 5-endo H, 2 x —CHCH$_2$CH$_3$), 2.13–2.23 (1H, m, 5-exo H), 3.05 (1H, d, J=4.6 Hz, 4-H), 3.18–3.24 (1H, m, 6-endo H), 3.30–3.33 (1H, m, 7-anti H), 3.39–3.47 (1H, m, 6-exo H), 3.48–3.58 (3H, m, 2-exo H, 2-endo H, 7-syn H), 4.11 (1H, d, J=9.4 Hz, 3′-H), 4.23 (1H, d, J=9.4 Hz, 3′-H), 5.01 (1H, t, J=4.5 Hz, —CHCH$_2$CH$_3$).

EXAMPLE 4

2'(R*)-Ethyl-4(R*)-spiro[1-azabicyclo[2.2.1]heptane-3(R*), 4'-[1,3]dioxolane] hydrogen oxalate and 2'(S*)-ethyl-4(R*)-spiro[1-azabicyclo[2.2.1]heptane-3(R*), 4'-[1,3]dioxolane] hydrogen oxalate

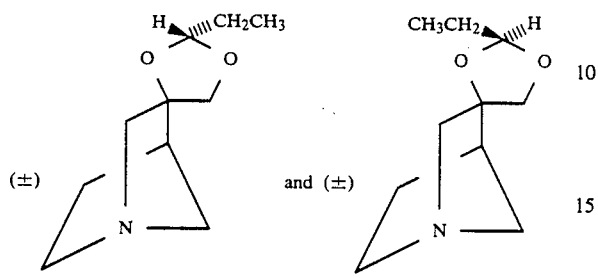

(a) Propionaldehyde diethyl acetal (7.42 g, 60 mmol) was added to a solution of the diol prepared according to Example 1(b) above and (±)camphor-10-sulphonic acid (4.18 g, 18 mmol) in dioxane (60 ml) and toluene (15 ml). The solution so obtained was heated under reflux for 5 hours, after which time the solvents were removed. The residue was partitioned between saturated aqueous potassium carbonate and dichloromethane, the layers separated and the aqueous extracted with dichloromethane. The combined organic layers were washed twice with water, dried over anhydrous sodium sulphate and evaporated to leave an orange-brown oil (1.36 g). This was dissolved in THF (25 ml), the solution cooled to −78° C., and a solution of borane in THF (1M, 8.97 ml) added. After 20 min, water (2 ml) was added, the mixture allowed to warm to room temperature, and the solvent evaporated. The residue was partitioned between water and dichloromethane, the organic layer dried over anhydrous sodium sulphate and evaporated to leave the crude diastereomeric borane complexes (800 mg). These were subjected to column chromatography on silica gel, eluting with a gradient of 0–2% methanol in dichloromethane to afford in order of elution, fraction A (320 mg) and fraction B (220 mg).

(b) Fraction A from (a) above (311 mg) was heated under reflux in ethylene glycol (10 ml) containing excess sodium methoxide for 1.5 hours. On cooling the mixture was diluted with water (40 ml) and the resulting solution extracted with four portions of dichloromethane. The combined organic layers were dried over anhydrous sodium sulphate and evaporated.

The residue was treated with an ethereal solution of oxalic acid to afford 2'(R*)-ethyl-4(R*)-spiro[1-azabicyclo[2.2.1]heptane-3(R*), 4'-[1,3]dioxolane] hydrogen oxalate as a colourless solid. m.p. 116°–117°; $R_f$=0.44 in 19:1 dichloromethane/methanol on alumina; (Found: C, 52.58; H, 6.96; N, 5.09. $C_{12}H_{19}NO_6$ requires: C, 52.74; H, 7.01; N, 5.13%); m/e 184 (M+1)+; δ (360 MHz, $D_2O$) 0.92 (3H, t, J=7.5 Hz, —$CHCH_2CH_3$), 1.66–1.76 (2H, m, —$CHCH_2CH_3$), 2.02–2.14 (1H, m, 5-H), 2.32–2.42 (1H, m, 5-H), 2.88 (1H, d, J=4.0 Hz, 4-H), 3.26–3.36 (4H, m, 2 x 6-H, 2 x 7-H), 3.46–3.58 (2H, m, 2 x 2-H), 3.82 (1H, d, J=9.3 Hz, 3'-H), 4.31 (1H, d, J=9.3 Hz, 3'-H), 5.09 (1H, t, J=4.4 Hz, —$CHCH_2CH_3$).

(c) Fraction B from (a) above was treated in an analogous manner to (b) above to give 2'(S*)-ethyl-4(R*)-spiro[1-azabicyclo[2.2.1]heptane-3(R*), 4'-[1,3]-dioxolane] hydrogen oxalate hydrate as a colourless solid, m.p. 115°–116° $R_f$=0.56 in 19:1 dichloromethane/methanol on alumina; (Found: C, 52.27; H, 6.90; N, 5.05. $C_{12}H_{19}NO_6.1H_2O$ requires: C, 52.40; H, 7.04; N, 5.09%); m/e 184 (M+1)+; δ (360 MHz, $D_2O$) 0.91 (3H, t, J=7.5 Hz, —$CHCH_2CH_3$), 1.64–1.76 (2H, m, —$CHCH_2CH_3$), 2.02–2.16 (1H, m, 5-H), 2.28–2.38 (1H, m, 5-H), 3.07 (1H, d, J=3.9 Hz, 4-H), 3.24–3.36 (4H, m, 2 x 6-H, 2 x 7-H), 3.46–3.56 (1H, m, 2-H), 3.64 (1H, dd, J=12.9, 2.8 Hz, 2-H), 3.91 (1H, d, J=8.6 Hz, 4'-H), 4.12 (1H, J=8.6 Hz, 4'-H), 5.06 (1H, t, J=4.7 Hz, —$CHCH_2CH_3$).

EXAMPLE 5

2'-Dimethyl-4(R*)-spiro[1-azabicyclo[2.2.1]heptane3(R*), 4'-[1,3]dioxolane] hydrogen oxalate

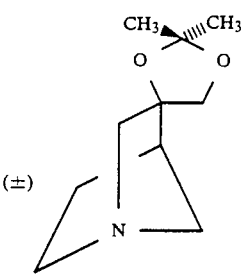

Boron trifluoride etherate (4 ml) was added dropwise over 5 min to a stirred suspension of the diol, prepared as in Example 4(b) above, (0.75 g, 5.2 mmol) in acetone (4 ml) contained in an ice-salt bath. The solid was seen to dissolve gradually and the ice bath removed after 0.5 hour. After stirring for a further 2.5 hours at room temperature, the reaction was quenched by addition of 20% aqueous potassium hydroxide (15 ml) and the resulting mixture stirred for 15 min before filtering through Hyflo to remove insoluble material. The filtrate was exhaustively extracted with dichloromethane, the organic layers combined and dried over anhydrous sodium sulphate and evaporated to leave a yellow oil (517 mg). Treatment with oxalic acid (252 mg) and recrystallisation of the solid produced from ethyl acetate-ether gave the title compound as a colourless solid (220 mg), m.p. 146°–147°; $R_f$=0.51 on alumina in 19:1 dichloromethane/methanol; (Found: C, 52.63; H, 6.94; N, 5.12. $C_{12}H_{19}NO_6$ requires: C, 52.74; H, 7.01; N, 5.13%); m/e 184 (M+1)+; δ (250 MHz, $D_2O$) 1.40 (3H, s, $CH_3$), 1.46 (3H, s, $CH_3$), 2.04–2.14 (1H, m, 5-H), 2.26–2.30 (1H, m, 5-H), 2.97 (1H, d, J=2.8 Hz, 4-H), 3.22–3.34 (4H, m, 2 x 6-H, 2 x 7-H), 3.46–3.62 (2H, m, 2 x 2-H), 3.96 (1H, d, J=6.4 Hz, 3-H), 4.25 (1H, d, J=6.4 Hz, 3'-H).

What is claimed is:

1. A compound of Formula II:

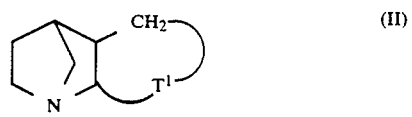

wherein —$T^1$— represents a group of formula

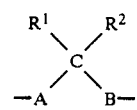

in which A and B independently represent oxygen or sulphur;

R¹ and R² independently represent hydrogen, straight-chained or branched $C_{2-4}$ alkyl or $C_{3-6}$ cycloalkyl and pharmaceutically acceptable salts thereof.

2. The compound according to claim 1 selected from the group consisting of

2'-ethylspiro[1-azabicyclo[2.2.1]heptane-3,4'-[1,3]dioxolane];

2'-propylspiro[1-azabicyclo[2.2.1]heptane-3,4'-[1,3]dioxolane];

2'-(1-methylethyl)spiro[1-azabicyclo[2.2.1]heptane-3,4'-[1,3]dioxolane]'

2'-cyclopropylspiro[1-azabicyclo[2.2.1]heptane-3,4'-[1,3]dioxolane];

2'-ethylspiro[1-azabicyclo[2.2.1]heptane-3,4'-[1,3]oxathiolane];

and pharmaceutically acceptable salt thereof.

3. The compound according to claim 1 wherein one of R¹ and R² represents hydrogen and the other represents ethyl.

4. A pharmaceutical composition comprising an effective amount of a compound according to claim 1 in association with a pharmaceutically acceptable carrier or excipient.

5. The pharmaceutical composition according to claim 4 further comprising a peripherally acting cholinergic antagonist.

6. A method for the treatment of neurological and mental disorders, which method comprises administering to a patient in need of such treatment an effective amount of a compound according to claim 1.

* * * * *